US012431000B2

(12) United States Patent
Hewitt et al.

(10) Patent No.: US 12,431,000 B2
(45) Date of Patent: Sep. 30, 2025

(54) DETECTING ALLERGENS USING INTERNET OF THINGS

(71) Applicant: International Business Machines Corporation, Armonk, NY (US)

(72) Inventors: Trudy L. Hewitt, Cary, NC (US); Christian Compton, Austin, TX (US); Mauro Marzorati, Lutz, FL (US); Jeremy R. Fox, Georgetown, TX (US)

(73) Assignee: International Business Machines Corporation, Armonk, NY (US)

( * ) Notice: Subject to any disclaimer, the term of this patent is extended or adjusted under 35 U.S.C. 154(b) by 114 days.

(21) Appl. No.: 18/588,441

(22) Filed: Feb. 27, 2024

(65) Prior Publication Data

US 2025/0273064 A1 Aug. 28, 2025

(51) Int. Cl.
*G08B 21/00* (2006.01)
*A61B 5/00* (2006.01)
*G08B 21/18* (2006.01)
*G16H 50/30* (2018.01)

(52) U.S. Cl.
CPC ............ *G08B 21/182* (2013.01); *A61B 5/411* (2013.01); *G16H 50/30* (2018.01)

(58) Field of Classification Search
CPC ....... G08B 21/182; G16H 50/30; A61B 5/411
See application file for complete search history.

(56) References Cited

U.S. PATENT DOCUMENTS

| | | | | |
|---|---|---|---|---|
| 4,637,405 A | * | 1/1987 | Brenman | A61N 1/0548 607/134 |
| 6,239,705 B1 | * | 5/2001 | Glen | G08B 21/028 340/573.4 |
| 7,947,508 B2 | * | 5/2011 | Tricca | A61B 5/0088 436/163 |
| 8,898,069 B2 | * | 11/2014 | Hood | A61B 5/411 705/2 |
| 9,766,959 B2 | * | 9/2017 | Faaborg | A61B 5/0533 |
| 10,235,859 B1 | * | 3/2019 | Hiles | A61B 5/18 |
| 10,307,051 B2 | * | 6/2019 | Ootsuki | A61B 3/102 |

(Continued)

OTHER PUBLICATIONS

Emily Matchar, Test Your Restaurant Meal for Allergens in Two Minutes (Year: 2015).*

(Continued)

*Primary Examiner* — Quang Pham
(74) *Attorney, Agent, or Firm* — Brandon Lorenz Stephens

(57) ABSTRACT

According to an embodiment of the present invention, a method for detecting allergens using smart tooth and IoT is provided. The method includes obtaining real-time environmental allergen context data, wherein the obtained real-time environmental allergen context data includes visual data and sensor data. Features are extracted from the obtained real-time environmental allergen context data, including at least one detected environmental allergen type, an environmental allergen exposure pathway, and an environmental allergen concentration. A real-time unique allergic reaction risk score is generated for a user based on analysis of a user allergic risk profile and the extracted features from the obtained real-time environmental allergen context data. A real-time warning is generated to the user when the generated unique allergic reaction risk score exceeds a predetermined threshold.

17 Claims, 3 Drawing Sheets

(56) References Cited

U.S. PATENT DOCUMENTS

| | | | | |
|---|---|---|---|---|
| 10,639,134 | B2* | 5/2020 | Shanjani | A61C 19/04 |
| 10,702,695 | B2 | 7/2020 | Costanzo | |
| 11,180,158 | B1* | 11/2021 | Lyle | B60W 40/08 |
| 2002/0061495 | A1* | 5/2002 | Mault | A61B 5/082 |
| | | | | 433/29 |
| 2010/0210033 | A1* | 8/2010 | Scott | G01N 33/543 |
| | | | | 422/69 |
| 2011/0318717 | A1* | 12/2011 | Adamowicz | G16H 20/60 |
| | | | | 434/127 |
| 2012/0072302 | A1* | 3/2012 | Chen | G06Q 30/0631 |
| | | | | 707/723 |
| 2012/0101847 | A1* | 4/2012 | Johnson | G16H 10/60 |
| | | | | 705/2 |
| 2013/0105565 | A1* | 5/2013 | Kamprath | G16H 20/60 |
| | | | | 235/375 |
| 2013/0268395 | A1* | 10/2013 | Sandow | G06Q 30/02 |
| | | | | 705/26.7 |
| 2014/0248574 | A1* | 9/2014 | Yoon | A61C 7/14 |
| | | | | 433/199.1 |
| 2014/0375462 | A1* | 12/2014 | Biondo | A61B 5/6893 |
| | | | | 340/576 |
| 2015/0019266 | A1* | 1/2015 | Stempora | G06Q 40/08 |
| | | | | 705/4 |
| 2015/0024421 | A1* | 1/2015 | Just | G01N 33/6869 |
| | | | | 435/7.94 |
| 2015/0025917 | A1* | 1/2015 | Stempora | G02B 27/0093 |
| | | | | 705/4 |
| 2015/0086594 | A1* | 3/2015 | Dewan | A61K 39/36 |
| | | | | 424/275.1 |
| 2015/0097687 | A1* | 4/2015 | Sloo | G01N 33/004 |
| | | | | 340/632 |
| 2015/0216641 | A1 | 8/2015 | Popa-Simil | |
| 2015/0281878 | A1* | 10/2015 | Roundtree | H04W 4/80 |
| | | | | 455/41.2 |
| 2015/0289790 | A1* | 10/2015 | Swenson | A61B 5/14507 |
| | | | | 600/344 |
| 2015/0379318 | A1* | 12/2015 | Herman | G06F 16/242 |
| | | | | 707/758 |
| 2016/0066776 | A1* | 3/2016 | Weiss | A61C 7/14 |
| | | | | 433/215 |
| 2016/0071393 | A1* | 3/2016 | Kaplan | A61B 5/162 |
| | | | | 340/539.12 |
| 2016/0113881 | A1* | 4/2016 | Sosin | A61K 39/145 |
| | | | | 424/241.1 |
| 2016/0135706 | A1* | 5/2016 | Sullivan | A61B 5/7275 |
| | | | | 600/509 |
| 2016/0367188 | A1* | 12/2016 | Malik | G16H 40/67 |
| 2017/0087363 | A1* | 3/2017 | Costanzo | A61N 1/0548 |
| 2017/0355377 | A1* | 12/2017 | Vijaya Kumar | B60W 50/0098 |
| 2018/0103339 | A1* | 4/2018 | Roundtree | H04W 4/023 |
| 2018/0105180 | A1* | 4/2018 | Fung | A61B 5/1122 |
| 2018/0116415 | A1* | 5/2018 | Karschnik | A47C 27/15 |
| 2018/0116604 | A1* | 5/2018 | Newberry | A61B 5/4845 |
| 2018/0154903 | A1* | 6/2018 | Song | B60W 60/0059 |
| 2018/0173230 | A1* | 6/2018 | Goldman-Shenhar | |
| | | | | B60W 50/08 |
| 2018/0178808 | A1* | 6/2018 | Zhao | B60N 2/20 |
| 2019/0008450 | A1* | 1/2019 | Gurievsky | A61B 5/4812 |
| 2019/0138690 | A1 | 5/2019 | Adams | |
| 2020/0152312 | A1* | 5/2020 | Connor | G06V 20/20 |
| 2020/0194125 | A1* | 6/2020 | Adolphus | H04W 4/029 |
| 2021/0009055 | A1* | 1/2021 | Brown | B60R 16/0237 |
| 2021/0030226 | A1* | 2/2021 | Broz | A47L 9/2857 |
| 2021/0082582 | A1* | 3/2021 | Barrett | A61B 5/74 |
| 2021/0186368 | A1* | 6/2021 | Kawecki | G08B 21/0453 |
| 2021/0225052 | A1 | 7/2021 | Marzorati | |
| 2021/0278387 | A1* | 9/2021 | Bistany | F24F 11/72 |
| 2022/0275966 | A1* | 9/2022 | Schoch | F24F 11/89 |
| 2022/0415476 | A1* | 12/2022 | Connor | G06V 20/20 |
| 2023/0210444 | A1* | 7/2023 | Schoof | A61B 5/7264 |
| | | | | 600/301 |
| 2023/0334552 | A1* | 10/2023 | Levin | G16H 20/60 |
| 2023/0335254 | A1* | 10/2023 | Vleugels | G16H 20/60 |
| 2024/0087745 | A1* | 3/2024 | Hsieh | G16H 50/20 |
| 2024/0268708 | A1* | 8/2024 | Lin | A61B 5/6815 |
| 2024/0285190 | A1* | 8/2024 | Bhowmik | A61B 5/112 |

OTHER PUBLICATIONS

Li et al., Oral Wearable Sensors Health Management Based on the Oral Cavity (Year: 2021).*

Anonymous, Smart Teeth with the Ability to Detect Warn & Correct Using Context-Dependent Measurements and Thresholds (Year: 2018).*

Sundhoro et al., An Electrochemical Molecularly Imprinted Polymer Sensor for Rapid and Selective Food Allergen Detection (Year: 2021).*

"AgraStrip® Allergen Test Kits", Food Samples, Instructional Video, YouTube, Romer Labs, downloaded from the Internet Feb. 5, 2024, < https://www.youtube.com/watch?v=qtA3LpGp3L8>, 3 pages.

"Food Allergen Testing Solutions", Romer Labs, downloaded from the Internet Feb. 5, 2024, <https://www.romerlabs.com/en/food-allergen-test-kits>, 7 pages.

"Food Allergies", FDA, downloaded from the Internet Feb. 5, 2024, 13 pages, <https://www.fda.gov/food/food-labeling-nutrition/food-allergies>.

"Smart Teeth with the Ability to Detect, Warn and Correct Using Context-Dependent Measurements and Thresholds", An IP.com Prior Art Database Technical Disclosure, Authors et al.: Disclosed Anonymously, IP.com No. IPCOM000255304D, IP.com Electronic Publication Date: Sep. 15, 2018, 4 pages.

"Smart Tooth Sensor to Regulate the Oral Habits Based on Neuro Transmitters Induction", An IP.com Prior Art Database Technical Disclosure, Authors et al.: Disclosed Anonymously, IP.com No. IPCOM000249516D, IP.com Electronic Publication Date: Mar. 2, 2017, 4 pages.

* cited by examiner

DETECTING ALLERGENS USING INTERNET OF THINGS

BACKGROUND

Exemplary embodiments of the present invention relate to detecting allergens, and more particularly, to detecting allergens using smart tooth and IoT.

Environmental allergens can cause discomforting and even life-threatening allergic reactions depending on various factors, such as the severity of an individual's allergic response, allergen concentration, availability of appropriate allergy medicine, and/or promptness of allergic reaction treatment. Environmental allergens are difficult to detect by the human senses alone. Even when exercising caution, environmental allergen exposure is typically inadvertent, latent, and/or cumulative. The danger posed by environmental allergen exposures and allergic reactions caused thereby is also frequently under appreciated. For example, food can be inadvertently cross contaminated with allergens. Food allergies cause someone to be sent to the emergency room (ER) every 3 minutes.

Although methods of chemical analysis for environmental allergen detection are available, these methods are often impractical for everyday use (e.g., costly, tedious, and/or delayed, etc.). Even equipped with a means to contemporaneously detect environmental allergens in everyday settings, small quantities/cumulations/synergy of environmental allergen exposures can be sufficient to cause severe allergy and hospitalization in some individuals.

SUMMARY

According to an embodiment of the present invention, a method for detecting allergens using smart tooth and IoT is provided. The method includes obtaining real-time environmental allergen context data, wherein the obtained real-time environmental allergen context data includes visual data and sensor data. Features are extracted from the obtained real-time environmental allergen context data, including at least one detected environmental allergen type, an environmental allergen exposure pathway, and an environmental allergen concentration. A real-time unique allergic reaction risk score is generated for a user based on analysis of a user allergic risk profile and the extracted features from the obtained real-time environmental allergen context data. A real-time warning is generated to the user when the generated unique allergic reaction risk score exceeds a predetermined threshold.

According to an exemplary embodiment of the present invention, a CPP for detecting allergens using smart tooth and IoT is provided. A computer program product (CPP) for detecting allergens using smart tooth and IoT. The CPP includes one or more computer-readable storage media and program instructions stored on the one or more non-transitory computer-readable storage media capable of performing a method. The method includes obtaining real-time environmental allergen context data, wherein the obtained real-time environmental allergen context data includes visual data and sensor data. Features are extracted from the obtained real-time environmental allergen context data, including at least one detected environmental allergen type, an environmental allergen exposure pathway, and an environmental allergen concentration. A real-time unique allergic reaction risk score is generated for a user based on analysis of a user allergic risk profile and the extracted features from the obtained real-time environmental allergen context data. A real-time warning is generated to the user when the generated unique allergic reaction risk score exceeds a predetermined threshold.

According to an exemplary embodiment of the present invention, a CS for detecting allergens using smart tooth and IoT is provided. A computer system (CS) for detecting allergens using smart tooth and IoT. The CS includes one or more computer processors, one or more computer-readable storage media, and program instructions stored on the one or more of the computer-readable storage media for execution by at least one of the one or more processors capable of performing a method. The method includes obtaining real-time environmental allergen context data, wherein the obtained real-time environmental allergen context data includes visual data and sensor data. Features are extracted from the obtained real-time environmental allergen context data, including at least one detected environmental allergen type, an environmental allergen exposure pathway, and an environmental allergen concentration. A real-time unique allergic reaction risk score is generated for a user based on analysis of a user allergic risk profile and the extracted features from the obtained real-time environmental allergen context data. A real-time warning is generated to the user when the generated unique allergic reaction risk score exceeds a predetermined threshold.

BRIEF DESCRIPTION OF THE DRAWINGS

The following detailed description, given by way of example and not intended to limit the exemplary embodiments solely thereto, will best be appreciated in conjunction with the accompanying drawings, in which.

Figure 1:
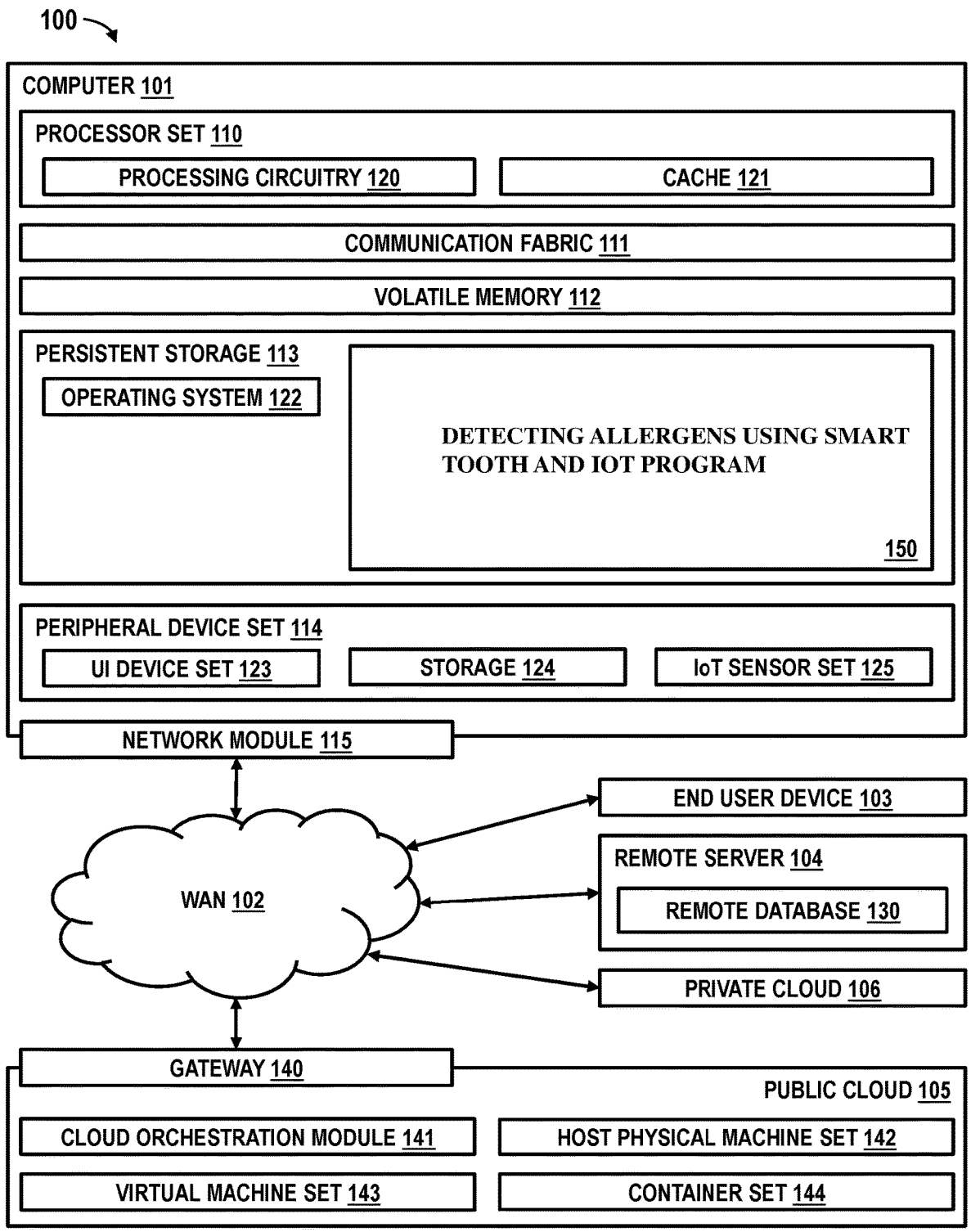
FIG. 1 illustrates a schematic diagram of a computing environment 100 including a detecting allergens using smart tooth and IoT program 150, in accordance with an exemplary embodiment of the present inventive concept.

It is to be understood that the included drawings are not necessarily drawn to scale/proportion. The included drawings are merely schematic examples to assist in understanding of the present invention and are not intended to portray fixed parameters. In the drawings, like numbering may represent like elements.

DETAILED DESCRIPTION

Exemplary embodiments of the present invention are disclosed hereafter. However, it shall be understood that the scope of the present invention is dictated by the claims. The disclosed exemplary embodiments are merely illustrative of the claimed invention. The present invention may be embodied in many different forms and should not be construed as limited to only the exemplary embodiments set forth herein. Rather, these included exemplary embodiments are provided for completeness of disclosure and to facilitate an understanding to those skilled in the art. In the detailed description, discussion of well-known features and techniques may be omitted to avoid unnecessarily obscuring the presented exemplary embodiments.

References in the specification to "one embodiment," "an embodiment," "an exemplary embodiment," etc., indicate that the embodiment described may include a particular feature, structure, or characteristic, but not every embodiment may necessarily include that feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether explicitly described.

In the interest of not obscuring the presentation of the exemplary embodiments of the present invention, in the following detailed description, some processing steps or operations that are known in the art may have been combined for presentation and for illustration purposes, and in some instances, may have not been described in detail. Additionally, some processing steps or operations that are known in the art may not be described at all. The following detailed description is focused on the distinctive features or elements of the present invention according to various exemplary embodiments.

The present inventive concept provides for a method, computer program product (CPP), and a computer system (CS) for detecting allergens using smart tooth and IoT. The present inventive concept detects environmental allergens, analyses factors such as the severity of an individual's allergic response, environmental allergen concentration, readiness of allergy medicine availability, and/or promptness of allergy treatment, and provides risk warnings/mitigation to a user. We propose an approach for reducing the barriers to use of monitoring devices capable of analysing environmental allergens, such as food intake, both before and while in a person's mouth. This device cohort can notify the user about actual and/or imminent exposure to an environmental allergen. It can also be customized to the user's specific tolerance and sensitivity to the allergen, as well as the probability of the presence of the allergen in the immediate future. The device can then alert the user about the environmental allergen exposure for immediate corrective action/consideration.

FIG. 1 illustrates a schematic diagram of a computing environment 100 including a detecting allergens using smart tooth and IoT program 150, in accordance with an exemplary embodiment of the present inventive concept.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer-readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer-readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Computing environment 100 contains an example of an environment for the execution of at least some of the computer code involved in performing the inventive methods, such as a detecting allergens using smart tooth and IoT program 150. In addition to block 150, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and block 150, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer-readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer-readable program instructions are stored in various types of computer-readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 150 in persistent storage 113.

COMMUNICATION FABRIC 111 is the signal conduction path that allows the various components of computer 101 to communicate with each other. Typically, this fabric is made of switches and electrically conductive paths, such as the switches and electrically conductive paths that make up buses, bridges, physical input/output ports and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface-type operating systems that employ a kernel. The code included in block 150 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer-readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economics of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

CLOUD COMPUTING SERVICES AND/OR MICROSERVICES (not separately shown in FIG. 1): private and public clouds 106 are programmed and configured to deliver cloud computing services and/or microservices (unless otherwise indicated, the word "microservices" shall be interpreted as inclusive of larger "services" regardless of size). Cloud services are infrastructure, platforms, or software that are typically hosted by third-party providers and made available to users through the internet. Cloud services facilitate the flow of user data from front-end clients (for example, user-side servers, tablets, desktops, laptops), through the internet, to the provider's systems, and back. In some embodiments, cloud services may be configured and orchestrated according to as "as a service" technology paradigm where something is being presented to an internal or external customer in the form of a cloud computing service. As-a-Service offerings typically provide endpoints with which various customers interface. These endpoints are typically based on a set of APIs. One category of as-a-service offering is Platform as a Service (PaaS), where a service provider provisions, instantiates, runs, and manages a modular bundle of code that customers can use to instantiate a computing platform and one or more applications, without the complexity of building and maintaining the infrastructure typically associated with these things. Another category is Software as a Service (SaaS) where software is centrally hosted and allocated on a subscription basis. SaaS is also known as on-demand software, web-based software, or web-hosted software. Four technological sub-fields involved in cloud services are: deployment, integration, on demand, and virtual private networks.

Figure 2:
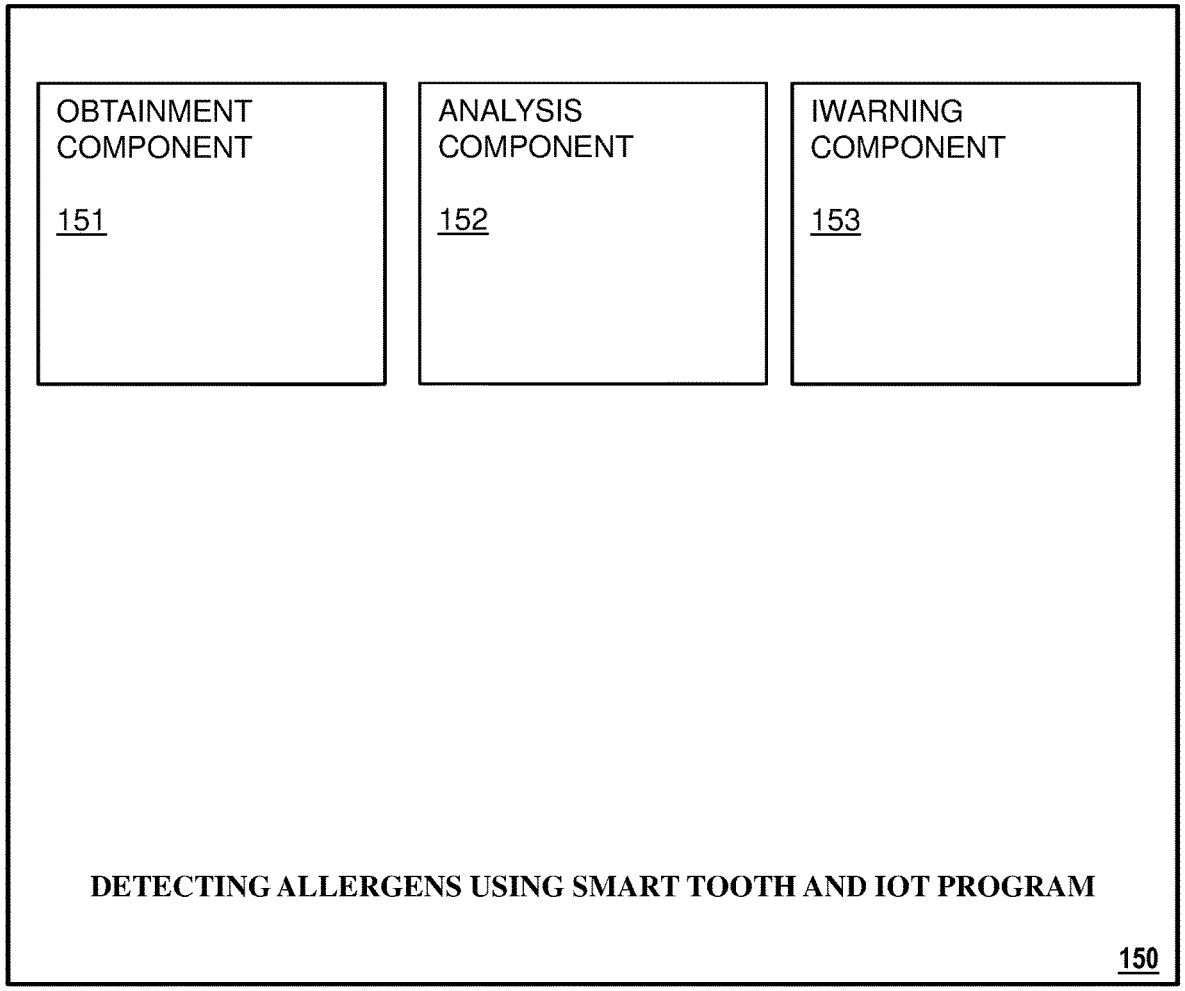
FIG. 2 illustrates a schematic diagram of a CS including the computing environment 100 and the detecting allergens using smart tooth and IoT program 150, in accordance with an exemplary embodiment of the present inventive concept.

FIG. 2 illustrates a schematic diagram of a CS including the computing environment 100 including the detecting allergens using smart tooth and IoT program 150, in accordance with an exemplary embodiment of the present inventive concept.

The detecting allergens using smart tooth and IoT program 150 can include an obtainment component 151, an analysis component 152, and/or a warning component 153.

The obtainment component 151 can be connected to at least one user sensor carried on the user's person. The user sensor can be connected to an IoT device of the user (e.g., a smartphone, smartphone accessory, fitness tracker, etc.) and/or a wearable sensor (e.g., removable, transportable, affixed, etc.), such as a thin film patch (e.g., a smart tooth). The smart tooth can include various sensors (e.g., chemical, thermal, visual, etc.). The smart tooth can analyze air composition, heat, and/or food, etc. In an embodiment, the smart tooth can be a wearable cap, brace, and/or a patch less which is less than the entire surface area of a predetermined tooth (e.g., an upper front incisor).

The obtainment component 151 can obtain prior/learned/crowd-sourced/real-time environmental allergen context data (e.g., user sensor data, visual data, location data, etc.). The environmental allergen context data can be obtained on a continuous basis, pursuant to manual user input (e.g., training and/or initiation), and/or autonomously upon a detected occurrence of a predetermined triggering condition (e.g., based on at least one extracted feature from the obtained environmental allergen context data that indicates actual/potential environmental allergen exposure). Environmental allergen context data sources can include a network search (e.g., webpages), relevant repositories (e.g., opted-in user electronic medical records, new allergy discoveries, medical journals, medical publications, food and drug administration (FDA) published content, environmental allergen databases, prior machine learning, food allergy knowledge corpus, etc.), user input, and/or connected devices (e.g., user/crowd-sourced IoT devices, smart teeth, miscellaneous sensors, fitness trackers, etc.). The obtainment component 151 can extract features from the obtained environmental allergen context data via machine learning, including but not limited to: user characteristics (e.g., health, age, weight, height, medications, health conditions, cavities, vitals, user environmental allergen exposures, user environmental allergen reactions, etc.), thresholds/delays of environmental allergen reactions and/or heat, locations/inventories of pharmacies/stores/users carrying allergy medications, planned/actual user location (e.g., route, destination, custom geographic area, region, city, street, address, business, venue, etc.), EMT response times for the planned/actual location, location of clinicians/clinics, planned/actual user location layout (e.g., dimensions, air volume, ventilation, outdoor/indoor seating, etc.), user estimated time of arrival (ETA) to planned/actual user location, planned/actual location activity (e.g., ordering, eating, sharing food, walking, working, etc.) and/or duration, planned/actual user location type (e.g., factory, restaurant, apartment, etc.), at least one environmental allergen type (e.g., food allergens, mold, pet hair, etc.), an environmental allergen exposure pathway (e.g., nose, mouth, lungs, skin contact, etc.), environmental allergen exposure symptoms (e.g., wheezing, anaphylaxis, asthma, vomiting, itching, sneezing, stomach cramps, swelling, light-headedness, hives, etc.), environmental allergen concentrations (e.g., ppm, density, mass, volume, potency over time, etc.), environmental allergen sources (e.g., objects, air, food, water, pets, etc.), environmental allergen exposures, object temperatures, and/or relative distances of environmental allergens/heat to a planned/actual user location.

For example, the obtainment component 151 obtains location data from a user's smartphone indicating a scheduled dinner and a GPS destination at a particular restaurant with an ETA of 1 hour. The user has input that they have a severe peanut allergy and asthma. Historical learning suggests that the user has a less severe shellfish sensitivity. The obtainment component 151 is triggered to obtain storefront dimensions (external and from pictures of the venue space), published textual data from the restaurant's web page (such as the menu and disclaimers thereon), user reviews, and prior crowd-sourced data from user's that dined at the restaurant. The obtainment component 151 extracts peanut and shellfish allergy warnings for certain menu offerings. User reviews additionally cite ambient indoor mold, cigarette smoke, and several other dishes suspected to have caused peanut allergies. Previous user smart teeth sensor data corroborated peanut contamination above a predetermined threshold in one of these certain menu offerings at least 45% of the time.

The analysis component 152 can analyze the extracted features from the obtained environmental allergen context data and/or obtain additional real-time environmental allergen context data. The analysis component 152 can map the extracted features to generate insights (e.g., determine relationships/causality/environmental allergen relative contributions/intensities/allergic reactions, etc.). The analysis component 152 can generate an overall/real-time/situational/location unique allergic reaction risk/burn score for the user based on analysis of the extracted features from the obtained real-time environmental allergen context data.

For example, the analysis component 152 analyzed the mapped extracted features from the environmental allergen context data and corroborates user reviews regarding cigarette smoke and indoor mold from a present diner's smart tooth and obtains values therefor. The analysis component 152 determines that, based on the restaurant dimensions/ventilation, and obtained ambient air values, the synergistic effect of the indoor mold and cigarette smoke is sufficient to cause a significant asthmatic response in the user based on their previous environmental allergen exposure incidents under similar circumstances and user characteristics. The user has input that they are carrying an EpiPen but not an inhaler. The analysis component 152 also determines that the user typically orders a dish known to contain peanut contamination above the predetermined threshold for the user.

The warning component 153 can alert the user of actual/potential environmental allergen exposures/ingestion pathways, risks (e.g., food, air, pets, etc.), risk mitigation (e.g., outdoor seating, avoiding concentrated environmental allergen sources/objects/spaces, masks, advised allergy medications, etc.), predicted allergic response symptoms, predicted allergic response thresholds/probabilities/durations, etc. via an interactive display on the user's IoT device. In an embodiment, the warning component 153 can modify a route/location/venue/business/time/reservation and/or provide special instructions. The warning component 153 can dynamically obtain/extract features from/analyze environmental allergen context data. The warning component 153 can advise a user to obtain an environmental sample prior to engaging in a predetermined activity (e.g., sampling food for self, sampling food for others, sampling air, sharing food, etc.). The smart tooth and/or IoT device can determine ambient/object temperatures, environmental allergen concentrations, potential cumulative/synergistic environmental allergen exposures, and compare them with the user allergic reaction risk/burn score. The warning component 153 can update warnings based on obtained real-time environmental data, extracted features, and analysis thereof, such as based on dynamic changes to actual/planned activity, location, route, vitals, latent environmental allergen exposures, detected environmental allergens, etc. The warning component 153 can predict the impact of risks, mitigated risks, and/or time-dependent risks and warn the user accordingly. The warning component 153 can generate duplicative, additional, and/or escalating warnings. In an embodiment, the warning component 153 can be connected to a user IoT device (e.g., smartphone) and provide annotated analyses and/or heat maps, such as with a virtual camera overlay and/or interface.

For example, the analysis component 153 advises the user to select outdoor dining and warns them about the menu items to avoid, particularly the dish they frequently order that has had peanut contamination. Thus, when the user arrives at the restaurant, they ask to be seated outdoors. However, the user disregards the potential peanut allergen warning and orders the dish with a 45% rate of peanut allergen contamination. The warning component 153 obtains visual data (e.g., the user taking a photo of the food with their smartphone and/or the smart tooth) of the dish. The warning component 153 determines that the emanating smoke, heatmap, and dish dimensions correlate with a heat that has a potential to burn their mouth. The warning component 153 advises the user to refrain from eating for 5 minutes or until a real-time change is detected. The warning component 153 further warns the user to obtain a small sample of the dish. The user raises a fork to their mouth without ingesting it. The warning component 153 detects fine airborne food particles contaminated with peanuts in the emanating smoke, but their concentration is just below a predetermined threshold. The warning component 153 thus subsequently advises the user to take a small bite first, which the user obliges. The peanut contamination is detected to be just below a predetermined threshold which would cause a unique allergic response in the user. However, the warning component 153 cautions the user that eating the entire dish could have a cumulative effect, and warns them to refrain from eating more than approximately 75% of the dish, as they are also sampling the shellfish dish of their fellow diner.

Figure 3:
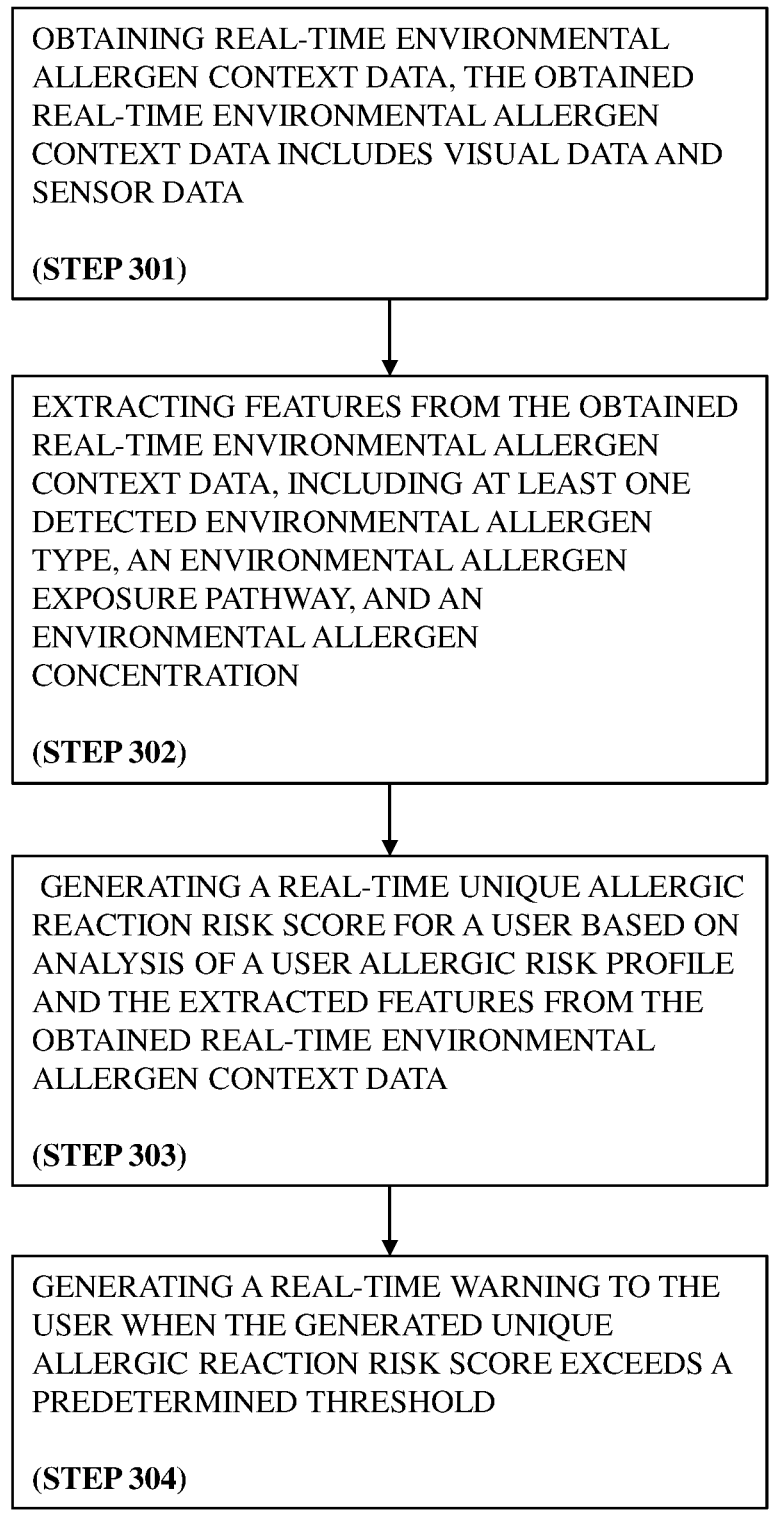
FIG. 3 illustrates a flowchart of a method of detecting allergens using smart tooth and IoT, in accordance with an exemplary embodiment of the present inventive concept.

FIG. 3 illustrates a flowchart of a method of detecting allergens using smart tooth and IoT, in accordance with an exemplary embodiment of the present inventive concept.

The method for detecting allergens using smart tooth and IoT can be performed by the detecting allergens using smart tooth and IoT program 150 and can include:
- obtaining real-time environmental allergen context data, wherein the obtained real-time environmental allergen context data includes visual data and sensor data (step 301);
- extracting features from the obtained real-time environmental allergen context data, including at least one detected environmental allergen type, an environmental allergen exposure pathway, and an environmental allergen concentration (step 302);
- generating a real-time unique allergic reaction risk score for a user based on analysis of a user allergic risk profile and the extracted features from the obtained real-time environmental allergen context data (step 303); and
- generating a real-time warning to the user when the generated unique allergic reaction risk score exceeds a predetermined threshold (step 304).

Based on the foregoing, a method, CPP, and a CS for detecting allergens using smart tooth and IoT have been disclosed. However, numerous modifications, additions, and substitutions can be made without deviating from the scope of the exemplary embodiments of the present invention. Therefore, the exemplary embodiments of the present invention have been disclosed by way of example and not by limitation.

What is claimed is:

1. A method executed by one or more processors of a computer system for detecting allergens using at least one sensor carried on a user and an Internet of Things (IoT) device of the user, the method comprising:
   obtaining, by the at least one sensor carried on the user and the IoT device of the user, real-time environmental allergen context data, wherein the obtained real-time environmental allergen context data includes visual data and sensor data;
   extracting features from the obtained real-time environmental allergen context data, including at least one detected environmental allergen type, an environmental allergen exposure pathway, and an environmental allergen concentration;
   generating a real-time unique allergic reaction risk score for the user based on analysis of a user allergic risk profile and the extracted features from the obtained real-time environmental allergen context data; and
   generating a real-time warning to the user when the generated unique allergic reaction risk score exceeds a predetermined threshold.

2. The method of claim 1, wherein the at least one sensor carried on the user includes a smart tooth.

3. The method of claim 1, wherein the at least one sensor carried on the user obtains environmental allergen particles in a location of the user.

4. The method of claim 1, wherein the obtained environmental allergen context data is obtained via at least one of: crowd-sourcing or via a network search.

5. The method of claim 1, wherein the generated warning preempts a unique allergic response in the user.

6. The method of claim 1, wherein the user allergic risk profile includes historic environmental allergen exposures, environmental allergen types, and environmental allergen severities.

7. A computer program product (CPP) for detecting allergens using at least one sensor carried on a user and an Internet of Things (IoT) device of the user, the CPP comprising:
   one or more computer-readable storage media and program instructions stored on the one or more computer-readable storage media to perform operations comprising:
   obtaining, by the at least one sensor carried on the user and the IoT device of the user, real-time environmental allergen context data, wherein the obtained real-time environmental allergen context data includes visual data and sensor data;
   extracting features from the obtained real-time environmental allergen context data, including at least one detected environmental allergen type, an environmental allergen exposure pathway, and an environmental allergen concentration;
   generating a real-time unique allergic reaction risk score for the user based on analysis of a user allergic risk profile and the extracted features from the obtained real-time environmental allergen context data; and
   generating a real-time warning to the user when the generated unique allergic reaction risk score exceeds a predetermined threshold.

8. The CPP of claim 7, wherein the at least one sensor carried on the user includes a smart tooth.

9. The CPP of claim 7, wherein the at least one sensor carried on the user obtains environmental allergen particles in a location of the user.

10. The CPP of claim 7, wherein the obtained environmental allergen context data is obtained via at least one of: crowd-sourcing or via a network search.

11. The CPP of claim 7, wherein the generated warning preempts a unique allergic response in the user.

12. The CPP of claim 7, wherein the user allergic risk profile includes historic environmental allergen exposures, environmental allergen types, and environmental allergen severities.

13. A computer system (CS) for detecting allergens using at least one sensor carried on a user and an Internet of Things (IoT) device of the user, the CS comprising:
   one or more computer processors, one or more computer-readable storage media, and program instructions stored on the one or more computer-readable storage media to cause the one or more computer processors to perform operations comprising:
   obtaining, by the at least one sensor carried on the user and the IoT device of the user, real-time environmental allergen context data, wherein the obtained real-time environmental allergen context data includes visual data and sensor data;

extracting features from the obtained real-time environmental allergen context data, including at least one detected environmental allergen type, an environmental allergen exposure pathway, and an environmental allergen concentration;

generating a real-time unique allergic reaction risk score for the user based on analysis of a user allergic risk profile and the extracted features from the obtained real-time environmental allergen context data; and generating a real-time warning to the user when the generated unique allergic reaction risk score exceeds a predetermined threshold.

14. The CS of claim 13, wherein the at least one sensor carried on the user includes a smart tooth.

15. The CS of claim 13, wherein the at least one sensor carried on the user obtains environmental allergen particles in a location of the user.

16. The CS of claim 13, wherein the obtained environmental allergen context data is obtained via at least one of: crowd-sourcing or via a network search.

17. The CS of claim 13, wherein the generated warning preempts a unique allergic response in the user.

* * * * *